United States Patent [19]
Beck et al.

[11] Patent Number: 5,488,194
[45] Date of Patent: Jan. 30, 1996

[54] SELECTIVE PRODUCTION OF PARA-DIALKYL SUBSTITUTED BENZENES AND CATALYST THEREFOR

[75] Inventors: Jeffrey S. Beck, Princeton; Ralph M. Dessau, Edison, both of N.J.

[73] Assignee: Mobil Oil Corp., Fairfax, Va.

[21] Appl. No.: 242,828

[22] Filed: May 16, 1994

[51] Int. Cl.⁶ .................................. C07C 5/52; C07C 2/66
[52] U.S. Cl. .................... 585/475; 585/446; 585/452; 585/467
[58] Field of Search .................. 585/475, 446, 585/452, 467

[56] References Cited

U.S. PATENT DOCUMENTS

| | | | |
|---|---|---|---|
| 2,722,504 | 11/1955 | Fleck | 196/52 |
| 2,904,607 | 9/1959 | Mattox et al. | 260/671 |
| 3,126,422 | 3/1964 | Planchard | 260/671 |
| 3,251,897 | 5/1966 | Wise | 260/671 |
| 3,413,374 | 11/1968 | Sato et al. | 260/672 |
| 3,598,878 | 8/1971 | Kovach et al. | 260/672 |
| 3,598,879 | 8/1971 | Kmecak et al. | 260/672 |
| 3,607,961 | 11/1971 | Kovach et al. | 260/672 R |
| 3,682,996 | 8/1972 | Kerr | 260/448 |
| 3,698,157 | 10/1972 | Allen et al. | 55/67 |
| 3,751,504 | 8/1973 | Keown et al. | 260/672 T |
| 3,751,506 | 8/1973 | Burress | 260/671 R |
| 4,029,716 | 6/1977 | Kaeding | 260/672 T |
| 4,060,568 | 11/1977 | Rodewald | 260/682 |
| 4,067,920 | 1/1978 | Kaeding | 260/671 M |
| 4,088,605 | 5/1978 | Rollmann | 252/455 Z |
| 4,090,981 | 5/1978 | Rodewald | 252/455 Z |
| 4,097,543 | 6/1978 | Haag et al. | 260/672 T |
| 4,100,219 | 7/1978 | Rodewald | 260/682 |
| 4,117,026 | 9/1978 | Haag et al. | 260/671 R |
| 4,127,616 | 11/1978 | Rodewald | 260/671 R |
| 4,145,315 | 3/1979 | Rodewald | 252/455 Z |
| 4,283,306 | 8/1981 | Herkes | 252/432 |
| 4,379,761 | 4/1983 | Olson et al. | 252/435 |
| 4,439,409 | 3/1984 | Puppe et al. | 423/328 |
| 4,465,886 | 8/1984 | Rodewald | 585/467 |
| 4,477,583 | 10/1984 | Rodewald | 502/71 |
| 4,548,914 | 10/1985 | Chu | 502/85 |
| 4,927,979 | 5/1990 | Yamagishi et al. | 568/791 |
| 4,950,835 | 8/1990 | Wang et al. | 585/467 |
| 4,954,325 | 9/1990 | Rubin et al. | 423/328 |
| 4,954,663 | 9/1990 | Marler et al. | 568/791 |
| 4,962,256 | 10/1990 | Le et al. | 585/467 |
| 4,962,257 | 10/1990 | Absil et al. | 585/475 |
| 4,992,606 | 2/1991 | Kushnerick et al. | 585/467 |
| 5,001,295 | 3/1991 | Angevine et al. | 585/467 |
| 5,043,512 | 8/1991 | Chu et al. | 585/481 |
| 5,173,461 | 12/1992 | Absil et al. | 502/62 |
| 5,236,575 | 8/1993 | Bennett et al. | 208/46 |
| 5,321,183 | 6/1994 | Chang et al. | 585/475 |
| 5,349,113 | 9/1994 | Chang et al. | 585/475 |
| 5,349,114 | 9/1994 | Lago et al. | 585/475 |
| 5,365,003 | 11/1994 | Chang et al. | 585/470 |
| 5,371,312 | 12/1994 | Lago et al. | 585/475 |

FOREIGN PATENT DOCUMENTS 0296582 12/1988 European Pat. Off. .

OTHER PUBLICATIONS

Chen, N. Y. et al., "Para-Directed Aromatic Reactions over Shape-Selective Molecular Sieve Zeolite Catalysts," Communications to the Editor, Journal of the American Chemical Society, 101:22, 6/83–6/84 (1979).

Pines, H., The Chemistry of Catalytic Hydrocarbon Conversions, 72–74 (1981).

Yashima, T. et al., "Alkylation on Synthetic Zeolites, 1. Alkylation of Toluene with Methanol," Journal of Catalysis, 16, 273–280 (1970).

Grandio, P. et al., "AP-catalyst processes make aromatics at low temperatures," Oil and Gas Journal, 62–69 (1971).

*Primary Examiner*—P. Achutamurthy
*Attorney, Agent, or Firm*—Alexander J. McKillop; Dennis P. Santini

[57] ABSTRACT

A process is provided for selective catalytic conversion of certain hydrocarbon feedstocks to product rich in para-dialkyl substituted benzenes. The catalyst required in the process comprises a crystalline material having the structure of PSH-3, MCM-22 or MCM-49, or a mixture of said crystalline materials, said crystalline material having been treated with one or more monomeric or polymeric siloxane compounds which decompose to oxide or non-oxide ceramic or solid-state carbon species.

17 Claims, No Drawings

SELECTIVE PRODUCTION OF PARA-DIALKYL SUBSTITUTED BENZENES AND CATALYST THEREFOR

BACKGROUND OF THE INVENTION

1. Field of the Invention

A process is provided for selective catalytic conversion of certain hydrocarbon feedstocks to product rich in para-dialkyl substituted benzenes. The catalyst required in the process comprises a crystalline material having the structure of PSH-3, MCM-22 or MCM-49, or a mixture of said crystalline materials, said crystalline material having been treated with one or more monomeric or polymeric siloxane compounds which decompose to oxide or non-oxide ceramic or solid-state carbon species.

2. Description of the Prior Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIB element, e.g., aluminum, is balanced by the inclusion in the crystal of a cation, e.g., an alkali metal or an alkaline earth metal cation. This can be expressed wherein the ratio of the Group IIIB element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (U.S. Pat. No. Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865; and 4,104,294 describe crystalline silicate of varying aluminum and metal content.

U.S. Pat. No. 4,439,409 refers to a composition of matter named PSH-3, useful as a catalyst component in the present invention, and its synthesis. U.S. Pat. No. 5,236,575 teaches MCM-49 crystalline material which is another zeolite useful as a catalyst component in the present invention. A composition of matter appearing to be identical to the PSH-3 of U.S. Pat. No. 4,439,409, but with additional structural components, is taught in European Patent Application 293,032. Crystalline MCM-22 is also useful in the present invention as a catalyst component, and its properties and synthesis are taught in U.S. Pat. No. 4,954,325.

Of the xylene isomers, i.e., ortho-, meta-, and para-xylene, meta-xylene is the least desired product, with para-xylene being the most desired product. Para-xylene is of particular value being useful in the manufacture of terephthalic acid which is an intermediate in the manufacture of synthetic fibers, such as "Dacron". Mixtures of xylene isomers, whether alone or in further admixture with ethylbenzene, generally containing a concentration of about 24 wt. % para-xylene in the equilibrium mixture, have previously been separated by expensive superfractionation and multistage refrigeration steps. Such process, as will be realized, has involved high operation costs and has a limited yield.

The term "shape-selective catalysis" describes unexpected catalytic selectivities in zeolites. The principles behind shape selective catalysis have been reviewed extensively, e.g., Chen, N.Y., et al., *Shape Selective Catalysis in Industrial Applications*, 36, Marcel Dekker, Inc. (1989). Within a zeolite pore, hydrocarbon conversion reactions such as isomerization, disproportionation, alkylation and transalkylation of aromatics are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective alkyl-substituted benzene disproportionation to para-dialkyl-substituted benzene.

A representative para-dialkyl-substituted benzene is para-xylene. The production of para-xylene is typically performed by methylation of toluene or by toluene disproportionation over a catalyst under conversion conditions. Examples include the reaction of toluene with methanol as described by Chen et al., *J. Amer. Chem. Soc.* 101, 6783 (1979), and toluene disproportionation, as described by Pines in *The Chemistry of Catalytic Hydrocarbon Conversions*, 72, Academic Press, NY (1981). Such methods typically result in the production of a mixture including para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

The equilibrium reaction for the conversion of toluene to xylene and benzene proceeds as follows:

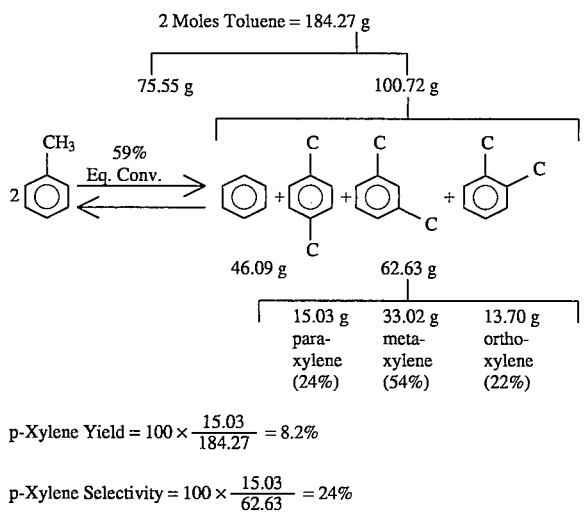

$$\text{p-Xylene Yield} = 100 \times \frac{15.03}{184.27} = 8.2\%$$

$$\text{p-Xylene Selectivity} = 100 \times \frac{15.03}{62.63} = 24\%$$

Disproportionation and alkylation of aromatics are mechanisms for production of para-dialkyl substituted benzenes, such as, for example, para-xylene. The equilibrium composition of xylene product from early catalytic processes is, as shown above, approximately 24 wt. % para-isomer, 54 wt. % meta-isomer, and 22 wt. % ortho-isomer. These early catalytic processes, as shown above, include disproportionation of aromatic hydrocarbons in the presence of zeolite catalysts, described by Grandio et al. in the *Oil and Gas Journal*, 69, 48 (1971). Also U.S. Pat. Nos. 3,126,422; 3,413,374; 3,598,878; 3,598,879; and 3,607,961 show vapor-phase disproportionation of toluene over various catalysts.

Various methods are known in the art for increasing the para-selectivity of zeolite catalysts. One such method is to modify the catalyst by treatment with a "selectivating agent". For example, U.S. Pat. Nos. 5,173,461; 4,950,835; 4,927,979; 4,477,583; 4,283,306; and 4,060,568 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Pat. No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon containing compounds.

U.S. Pat. No. 4,097,543 teaches a process for selective toluene disproportionation to yield increased para-xylene utilizing a specific crystalline zeolite catalyst, e.g., ZSM-5, which has undergone prior treatment to deposit a controlled amount of carbon coke thereon.

In addition to the above patents, U.S. Pat. No. 2,904,607 refers to alkylation of aromatic hydrocarbons with an olefin in the presence of a crystalline metalloaluminosilicate having uniform pore openings of about 6 to 15 Angstrom units. U.S. Pat. No. 3,251,897 describes alkylation of aromatic hydrocarbons in the presence of X- or Y-type crystalline aluminosilicate zeolites, specifically said zeolites wherein the cation is rare earth and/or hydrogen. U.S. Pat. Nos. 3,751,504 and 3,751,506 describe vapor phase alkylation of aromatic hydrocarbons with olefins, e.g., benzene with ethylene, in the presence of, for example, a ZSM-5 zeolite catalyst.

The alkylation of toluene with methanol in the presence of a cation-exchanged zeolite Y has been described by Yashima et al. in the *Journal of Catalysis*, 16, 273–280 (1970). The workers reported selective production of para-xylene over the approximate temperature range of 200° C. to 275° C., with the maximum yield of para-xylene in the mixture of xylenes, i.e., about 50 percent of the xylene product mixture, being observed at 225° C. Higher temperatures were reported to result in an increase in the yield of meta-xylene and a decrease in the production of para- and ortho-xylenes. U.S. Pat. No. 3,965,210 describes alkylation of toluene with methanol in the presence of a crystalline aluminosilicate zeolite, such as ZSM-5, which has been modified by contact with a polymer made up of meta-carborane units connected by siloxane units to selectively yield para-xylene. These latter catalysts have, however, suffered from the serious deficiency of loss of selectivity upon air regeneration. This is attributable to breakage of carbon-silicon bonds upon exposure to the high temperature of regeneration giving rise to isolated clusters of silica on the zeolite surface rather than the extensive surface coverage afforded by the technique described herein.

U.S. Pat. Nos. 4,029,716 and 4,067,920 teach use of a specific catalyst, e.g., ZSM-5 or ZSM-11, which has been pretreated with a particular boron compound to produce para-xylene by alkylating toluene with an olefin. U.S. Pat. No. 4,117,026 teaches selective production of para-dialkyl substituted benzenes over catalyst comprising a large crystal zeolite, e.g., ZSM-5, having certain sorption characteristics.

U.S. Pat. No. 2,722,504 describes a catayst of an activated oxide such as silica gel having a thin layer of a silicone polymer deposited thereon to increase the organophilic character of the contact surface and, as such, seeks to avoid silica deposition.

Crystalline aluminosilicate zeolites, modified by reaction with an organic substituted silane, have been described in U.S. Pat. Nos. 3,682,996 and 3,698,157. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 crystalline aluminosilicate zeolite modified by treatment with an organic-radical substituted silane is described, together with the use of such modified zeolite in chromatographic separation of the compounds in a $C_8$ aromatic feedstock.

U.S. Pat. No. 4,145,315 discloses a method for the production of silica-modified zeolite catalysts which are prepared by contacting the specific zeolite with an organic solvent solution such as hexane, of a silcone fluid, distillation of the hexane, and air calcination of the zeolite residue.

Silica-modified catalysts are shown in U.S. Pat. Nos. 4,379,761; 4,100,219; 4,090,981; and 4,127,616. In each instance the silica modification results from interaction of the zeolite portion of the catalyst with an organic solution comprising a silica source such as a silicone. U.S. Pat. No. 4,465,886 teaches selective conversion of hydrocarbon compounds to product rich in para-dialkyl substituted benzenes over catalyst comprising a zeolite, e.g., ZSM-5, ZSM-5/ZSM-11 intermediate, ZSM-11, ZSM-12, ZSM-23, ZSM-35, ZSM-38, or ZSM-48, having deposited thereon a coating of silica which covers exclusively the external surface of the zeolite.

U.S. Pat. No. 4,088,605 shows altering a crystallization medium to substantially eliminate aluminum during crystallization in order to synthesize a zeolite with a coating of silica.

Catalysts comprising MCM-22 or PSH-3, two crystalline materials useful in the present invention, are taught for use in U.S. Pat. Nos. 4,954,663; 4,962,256; 4,962,257; 4,992,606; and 5,001,295, for aromatic compound alkylation or disproportionation in general. U.S. Pat. No. 5,043,512 teaches converting alkylaromatic compounds by isomerization over catalyst comprising crystalline MCM-22.

SUMMARY OF THE INVENTION

In accordance with the present invention, there has been discovered a process for the selective production of para-dialkyl substituted benzenes. The catalyst required for the present process comprises a porous crystalline material having the structure of PSH-3, MCM-22 or MCM-49, or a mixture of said crystalline materials, having been treated with one or more monomeric or polymeric siloxane compounds which decompose to oxide or non-oxide ceramic or solid-state carbon species. The crystalline material employed has an activity, in terms of Alpha Value, of from about 10 to about 2000, and a xylene sorption capacity greater than about 1 gram/100 grams of crystalline material.

The above catalyst has been found to be particularly useful in the selective production of para-dialkyl substituted benzenes containing alkyl groups of 1 to 4 carbon atoms, such as para-xylene, by conversion in the presence thereof, of a hydrocarbon precursor such as a mono alkyl-substituted benzene having 1 to 4 carbon atoms in the alkyl substituent or a mixture of such precursor or benzene with an alkylating agent containing from 1 to 4 carbon atoms. Typical mechanisms of the above conversion process are the disproportionation of toluene and the alkylation of benzene or toluene with an alkylating agent, e.g., methanol.

DESCRIPTION OF SPECIFIC EMBODIMENTS

The crystalline material component of the catalyst for use herein is characterized by its unusual structure and its particular activity and sorption properties. Thus, the crystalline material for use herein has (i) the structure of a zeolitic material selected from the group consisting of PSH-3, MCM-22, MCM-49, and a mixture thereof; (ii) an activity, in terms of Alpha Value, of from about 10 to about 2000, preferably from about 100 to about 600; and (iii) a para-xylene sorption capacity greater than about 1 gram/100 grams of crystalline material, preferably from about 5 to about 10 grams/100 grams of crystalline material, the sorption capacity measured at 120° C. and a p-xylene pressure of 4.5±0.8 mm of mercury.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec $^{-1}$). The Alpha Test is described in U.S. Pat. No. 3,354,078; in the *Journal of Catalysis*, 4,527 (1965); 6,278 (1966); and 61,395 (1980), each incorporated herein by reference as to that description. The experimental conditions of the test used herein include a constant temperature of 538° C. and a variable flow rate as described in detail in the *Journal of Catalysis*, 61,395.

The measurement of p-xylene sorption capacity is conveniently carried out gravimetrically in a thermal balance. In particular, it has been found that an equilibrium sorption capacity of p-xylene of at least about 1 gram/100 grams of zeolite, preferably from about 5 to about 10 grams/100 grams of zeolite, measured at 120° C. and a p-xylene pressure of 4.5±0.8 mm of mercury is required in order to achieve the desired selective production of para-dialkyl substituted benzenes in this process.

The crystalline material component of the catalyst for use herein must have the structure of one selected from the group consisting of PSH-3, MCM-22, and MCM-49. Mixtures of such crystalline materials may also be used. These materials have partial, large-pore structure characteristics and exhibit an unusual amount of external acid activity, possibly due to the presence of large, 12-membered ring exterior pockets which do not connect with the internal pore system. The internal pore structures of this class of crystals are believed to consist of two-dimensional, 10-membered ring systems which intersect to access large supercages. The total catalytic activity of these materials is, therefore, believed to be a composite of 10-membered ring, 12-membered ring pocket, and supercage activity. These large-pore characteristics suggest that effecting shape selectivity in these materials would be difficult. However, modification of these materials with molecular or polymeric species whose molecular diameters are chosen to selectively alter access to one or more of these catalytically active sites produces novel catalytic behavior, as exemplified below.

In its calcined form, a synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
|---|---|
| 12.36 ± 0.4 | m–vs |
| 11.03 ± 0.2 | m–s |
| 8.83 ± 0.14 | m–vs |
| 6.18 ± 0.12 | m–vs |
| 6.00 ± 0.10 | w–m |
| 4.06 ± 0.07 | w–s |
| 3.91 ± 0.07 | m–vs |
| 3.42 ± 0.06 | vs |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | w–m |
| 22.1 ± 1.3 | w |
| 12.36 ± 0.4 | m–vs |
| 11.03 ± 0.2 | m–s |
| 8.83 ± 0.14 | m–vs |

TABLE B-continued

| Interplanar d-Spacing (A) | Relative Intensity, $I/I_o \times 100$ |
|---|---|
| 6.18 ± 0.12 | m–vs |
| 6.00 ± 0.10 | w–m |
| 4.06 ± 0.07 | w–s |
| 3.91 ± 0.07 | m–vs |
| 3.42 ± 0.06 | vs |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | m–vs |
| 11.03 ± 0.2 | m–s |
| 8.83 ± 0.14 | m–vs |
| 6.86 ± 0.14 | w–m |
| 6.18 ± 0.12 | m–vs |
| 6.00 ± 0.10 | w–m |
| 5.54 ± 0.10 | w–m |
| 4.92 ± 0.09 | w |
| 4.64 ± 0.08 | w |
| 4.41 ± 0.08 | w–m |
| 4.25 ± 0.08 | w |
| 4.10 ± 0.07 | w–s |
| 4.06 ± 0.07 | w–s |
| 3.91 ± 0.07 | m–vs |
| 3.75 ± 0.06 | w–m |
| 3.56 ± 0.06 | w–m |
| 3.42 ± 0.06 | vs |
| 3.30 ± 0.05 | w–m |
| 3.20 ± 0.05 | w–m |
| 3.14 ± 0.05 | w–m |
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

Most specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | w–m |
| 22.1 ± 1.3 | w |
| 12.36 ± 0.4 | m–vs |
| 11.03 ± 0.2 | m–s |
| 8.83 ± 0.14 | m–vs |
| 6.86 ± 0.14 | w–m |
| 6.18 ± 0.12 | m–vs |
| 6.00 ± 0.10 | w–m |
| 5.54 ± 0.10 | w–m |
| 4.92 ± 0.09 | w |
| 4.64 ± 0.08 | w |
| 4.41 ± 0.08 | w–m |
| 4.25 ± 0.08 | w |
| 4.10 ± 0.07 | w–s |
| 4.06 ± 0.07 | w–s |
| 3.91 ± 0.07 | m–vs |
| 3.75 ± 0.06 | w–m |
| 3.56 ± 0.06 | w–m |
| 3.42 ± 0.06 | vs |
| 3.30 ± 0.05 | w–m |
| 3.20 ± 0.05 | w–m |
| 3.14 ± 0.05 | w–m |
| 3.07 ± 0.05 | w |
| 2.99 ± 0.05 | w |
| 2.82 ± 0.05 | w |
| 2.78 ± 0.05 | w |

TABLE D-continued

| Interplanar d-Spacing (A) | Relative Intensity, $I/I_o \times 100$ |
|---|---|
| 2.68 ± 0.05 | w |
| 2.59 ± 0.05 | w |

Examples of such above porous crystalline materials include the PSH-3 composition of U.S. Pat. No. 4,439,409 and MCM-22 of U.S. Pat. No. 4,954,325, each incorporated herein by reference.

Zeolite MCM-22 has a composition involving the molar relationship $$X_2O_3:(n)YO_2,$$

wherein X is a trivalent element such as aluminum, boron, iron, and/or gallium, preferably aluminum; Y is a tetravalent element such as silicon and/or germanium, preferably silicon; and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1) Na_2O:(1-4)R:X_2O_3:(n)YO_2$$

wherein R is an organic component, e.g., hexamethyleneimine. The Na and R components are associated with the zeolite as a result of their presence during crystallization and are easily removed by post-crystallization methods hereinafter more particularly described.

Zeolite MCM-22 is thermally stable and exhibits a high surface area greater that about 400 $m^2/gm$ as measured by the BET (Bruenauer, Emmet, and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include hydrogen ions and hydrogen precursor, e.g., ammonium, ions. In its calcined form, zeolite MCM-22 appears to be made up of a single crystal phase with little or no detectable impurity crystal phases and has an X-ray diffraction pattern including the lines listed in above Tables A–D.

The crystalline material MCM-49 for use as catalyst component in this invention is described in U.S. Pat. No. 5,236,575, entirely incorporated herein by reference, and has a composition involving the molar relationship:

$$X_2O_3:(n)YO_2,$$

wherein X is a trivalent element, such as aluminum, boron, iron and/or gallium, preferably aluminum; Y is a tetravalent element such as silicon, titanium, and/or germanium, preferably silicon; and n is less than about 35, e.g., from 2 to less than about 35, usually from about 10 to less than about 35, more usually from about 15 to about 31. In the as-synthesized form, the material has a formula, on an anhydrous basis and in terms of moles of oxides per n moles of $YO_2$, as follows:

$(0.1–0.6)M_2O:(1–4)R:X_2O_3:(n)YO_2$ wherein M is an alkali or alkaline earth metal, and R is an organic moiety. The M and R components are associated with the material as a result of their presence during crystallization, and are easily removed by post-crystallization methods hereinafter more particularly described.

The MCM-49 crystalline material for use in the invention is thermally stable and in the calcined form exhibits high surface area (greater than 400 m²/gm) and unusually large sorption capacity when compared to previously described materials having similar X-ray diffraction patterns. To the extent desired, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB, and VIII of the Periodic Table of the Elements.

In the as-synthesized form, the crystalline MCM-49 material for use in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table E below:

TABLE E

| Interplanar d-Spacing (A) | Relative Intensity, $I/I_o \times 100$ |
|---|---|
| 13.15 ± 0.26 | w–s* |
| 12.49 ± 0.24 | vs |
| 11.19 ± 0.22 | m–s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

The X-ray diffraction peak at 13.15±0.26 Angstrom Units (A) is usually not fully resolved for MCM-49 from the intense peak at 12.49±0.24, and is observed as a shoulder of this intense peak. For this reason., the precise intensity and position of the 13.15±0.26 Angstroms peak are difficult to determine within the stated range.

In its calcined form, the crystalline MCM-49 material for use in the invention is a single crystal phase with little or no detectable impurity crystal phases having an X-ray diffraction pattern which is not easily distinguished from that of MCM-22, another crystal useful in this invention, but is readily distinguishable from the patterns of other known crystalline materials. The X-ray diffraction pattern of the calcined form of MCM-49 includes the lines listed in Table F below:

TABLE F

| Interplanar d-Spacing (A) | Relative Intensity, $I/I_o \times 100$ |
|---|---|
| 12.41 ± 0.24 | vs |
| 11.10 ± 0.22 | s |
| 8.89 ± 0.17 | m–s |
| 6.89 ± 0.13 | w |
| 6.19 ± 0.12 | m |
| 6.01 ± 0.12 | w |
| 5.56 ± 0.11 | w |

TABLE F-continued

| Interplanar d-Spacing (A) | Relative Intensity, $I/I_o \times 100$ |
|---|---|
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w–m |
| 3.92 ± 0.08 | w–m |
| 3.75 ± 0.07 | w–m |
| 3.57 ± 0.07 | w |
| 3.43 ± 0.07 | s–vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

The X-ray diffraction data presented herein were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 with similar materials, e.g., MCM-22 and PSH-3.

The significance of differences in the X-ray diffraction patterns of these materials can be explained from a knowledge of the structures of the materials. MCM-22 and PSH-3 are members of an unusual family of materials because, upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members. An examination of the X-ray diffraction patterns of both precursor and calcined forms shows a number of reflections with very similar position and intensity, while other peaks are different. Some of these differences are directly related to the changes in the axial dimension and bonding.

The as-synthesized MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at~13.5 Angstroms and~6.75 Angstroms in precursor MCM-22, at~12.8 Angstroms and~6.4 Angstroms in as-synthesized MCM-49, and at~12.6 Angstroms and~6.30 Angstroms in the calcined MCM-22. Unfortunately, the~12.8 Angstroms peak in MCM-49 is very close to the intense~12.4 Angstroms peak observed for all three materials, and is frequently not fully separated from it. Likewise, the~12.6 Angstroms peak of the calcined MCM-22 material is usually only visible as a shoulder on the intense~12.4 Angstroms peak. U.S. Pat. No. 5,236,575 details these differences, especially FIGS. 1 and 8, and is incorporated herein by reference in its entirety. Because the~ 6.4 Angstroms peak is unobscured in MCM-49, it was chosen as a better means of distinguishing MCM-49 from the calcined forms of MCM-22 and PSH-3 rather than the much stronger~12.8 Angstroms peak. Table E lists the diffraction peaks characteristic of MCM-49.

Synthesis of PSH-3, MCM-22, and MCM-49 is detailed in U.S. Pat. Nos. 4,439,409; 4,954,325; and 5,236,575, respectively, each patent incorporated herein by reference in its entirety.

Prior to its use as catalyst in the present process, the crystalline material should be subjected to thermal treatment to remove part or all of any organic constituent present therein. This thermal treatment is generally performed by heating at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

The crystalline material MCM-22, PSH-3, or MCM-49 for use herein must be treated with molecular or polymeric selectivating agent species which alter the diffusion properties of the crystal to be as above defined. This results in enhanced selectivity for the process of the invention. Species used for modification may include, for example, silicon-containing compounds such as monomeric or polymeric siloxanes, other main group species (e.g., those containing Ge, B, P, Mg, and/or Sb) which decompose to oxide or non-oxide ceramics, or solid-state carbon species. U.S. Pat. No. 5,120,692, incorporated herein by reference in its entirety, demonstrates examples of suitable species for use herein.

Useful selectivating agents include siloxanes which can be characterized by the general formula:

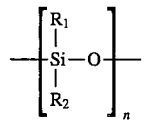

where $R_1$ is hydrogen; halogen; hydroxyl; alkyl or halogenated alkyl of from 1 to 10 carbons; or aryl, halogenated aryl, aralkyl, halogenated aralkyl, alkaryl or halogenated alkaryl of from 6 to 20 carbons. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other, more preferred silicon compounds, including silanes, alkoxy silanes, and organoamine silanes, may also be utilized. These useful silicon-containing selectivating agents include silanes characterizable by the general formula:

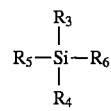

where $R_3$, $R_4$, $R_5$ and $R_6$ are independently selected from the group consisting of hydrogen; hydroxyl; halogen; alkyl of from 1 to 10 carbons; halogenated alkyl of from 1 to 10 carbons; alkoxy; aryl, halogenated aryl, aralkyl, halogenated aralkyl, alkaryl, or halogenated alkaryl of from 6 to 20 carbons; and organoamine groups of from 3 to 9 carbons. Most preferably $R_3$, $R_4$, $R_5$ and $R_6$ are independently selected from the group consisting of —$N(CH_3)_3$, —$N(C_2H_5)_3$ and —$N(C_3H_7)_3$. Mixtures of these compounds may also be used.

Such compounds are preferred because of their amphiphilic character, allowing their dissolution, or at least emulsification, in aqueous carriers, as well as taking advantage of the hydrophobic character of the zeolite on which the silicon compounds are being deposited.

The kinetic diameter of the high efficiency, p-dialkyl aromatic selectivating agent may be larger than the zeolite pore diameter, in order to avoid entry of the selectivating agent into the pore and any concomitant reduction in the internal activity of the catalyst. When a silicon compound is used that is of a size small enough to enter the pores of the catalyst crystal, it is desirable to use the sodium form of the zeolite rather than the hydrogen form.

For use in the present invention, the zeolite, either incorporated with a binder or in unbound form, is impregnated with the selectivating agent, preferably between about two and about six times. In each phase of the selectivation treatment, the selectivating agent is deposited on the external surface of the catalyst by any suitable method. For example, the selectivating agent may be dissolved in a carrier, mixed with the catalyst and then dried by evaporation or vacuum distillation. This method is termed "impregnation". The molecular sieve may be contacted with the silicon compound at a molecular sieve/silicon compound weight ratio of from about 100/1 to about 1/100.

The silicon compound employed may be in the form of a solution, an emulsion, a liquid or a gas under the conditions of contact with the zeolite. Not wishing to be bound by theory, it is believed that the deposited silicon compound extensively covers, and resides substantially exclusively on, the external surface of the molecular sieve. Examples of methods of depositing silicon on the surface of the zeolite are found in U.S. Pat. Nos. 4,090,981; 4,127,616; 4,465,886; and 4,477,583 to Rodewald, which are incorporated by reference herein. Further examples of silicon deposition on zeolite surfaces are described in Nakajima, H. et al., Sekiyu Gakkaishi, 35(2) (1992), and U.S. Pat. No. 4,950,835 to Wang et al.

The catalysts for use in the present invention are ex situ selectivated by multiple coatings with the high efficiency, para-selectivating agent, each coating followed by calcination, and optionally trim-selectivation with additional high efficiency para-selectivating agent. As used herein, the term "high efficiency, para-selectivating agent" is used to indicate substances which will increase the para-selectivity of a catalytic molecular sieve to the stated levels in alkylbenzene disproportionation while maintaining commercially acceptable levels of alkylbenzene to dialkylbenzene conversion.

Following each deposition of the silicon compound, the catalyst is calcined to decompose the molecular or polymeric species to a solid state species. The catalyst may be calcined at a rate of from about 0.2° C./minute to about 5° C./minute to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the containing medium, the degree to which the zeolite has been dried prior to contact with the silicon compound, and calcination of the zeolite.

After the selectivation sequence, the catalyst is preferably exchanged at least once with $NH_4^+$ ions by immersing the catalyst in a solution containing $NH_4^+$ ions. Most preferably the concentration of $NH_4^+$ ions is approximately 1M. The $NH_4^+$ solution may include various inorganic anions, most preferably $NO_3^{3-}$. Most preferably, the $NH_4^+$ exchange is performed three times.

After the $NH_4^+$ exchange sequence, if any, the catalyst may be subjected to steam treatment at a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours. The selectivated molecular sieve catalyst, with or without binder, can show improved selectivity upon steaming. Alternatively, excessive steaming can be detrimental to a selectivated catalyst.

The catalyst for use herein can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying, or partially dried and then extruded.

It may be desired to incorporate the crystalline material with another material which is resistant to the temperatures and other conditions employed in the condensation process of this invention. Such materials include active and inactive materials and synthetic or naturally occurring zeolites as well as inorganic materials such as clay, silica, and/or metal oxides such as alumina, magnesia, zirconia, thoria, beryllia, and/or titania. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that the products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin families which include the subbentonites and the kaolins commonly known as Dixie, McNamee, Georgia, and Florida clays, or others in which the main mineral constituent is halloysite, kaolinite, dickite, nacrite, or anauxite. Such clays can be used in the raw state as originally mined or initially subjected to calcination, acid treatment, or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. It may also be advantageous to provide at least a part of the foregoing matrix materials in colloidal form to facilitate extrusion of the bound catalyst components.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The modified zeolite catalysts for use in the invention facilitate the conversion of alkylbenzene compounds to provide dialkyl-substituted benzene products which are highly enriched in the para-dialkyl-substituted benzene isomer. Conversion reactions of this type include aromatics alkylation, transalkylation and disproportionation. Alkylation of aromatics in which the catalyst of the invention can be used are described, for example, in U.S. Pat. Nos. 3,755,483; 4,086,287; 4,117,024; and 4,117,026, which are incorporated herein by reference.

The modified catalyst for use herein has been found to be particularly useful in the selective production of para-dialkyl-substituted benzenes containing alkyl groups of 1 to 4 carbon atoms, such as para-xylene. Such processes are typified by the disproportionation, in the presence of the modified catalyst, of a hydrocarbon precursor, typically a monoalkyl-substituted benzene having 1 to 4 carbon atoms in the alkyl substituent.

As described in U.S. Pat. No. 3,755,483, aromatic hydrocarbons such as benzenes, naphthalenes, anthracenes and substituted derivatives thereof, e.g., toluene and xylene, may be alkylated with alkylating agents such as olefins ethylene, propylene, dodecylene, and formaldehyde, alkyl halides, and alkyl alcohols with 1 to 24 carbons under vapor phase conditions including a reactor inlet temperature up to about 482° C., with a reactor bed temperature up to about 566° C., at a pressure of about atmospheric to about 3000 psig, a mole ratio of aromatic compound/alkylating agent of from about 1:1 to about 20:1, and a WHSV of 20 to 3000 hr$^{-1}$ over catalyst comprising ZSM-12.

As described in U.S. Pat. No. 4,086,287, monoalkylbenzenes having alkyls of 1–2 carbons, such as toluene and ethylbenzene, may be ethylated to produce a para-ethyl derivative, e.g., para-ethyltoluene at a temperature of from about 250° C. to about 600° C., a pressure of 0.1 atmospheres to 100 hr$^{-1}$ atmospheres, a weight hourly space velocity (WHSV) of 0.1 to 100 hr$^{-1}$, and a ratio of feed/ ethylating agent of 1 to 10 over a catalyst having an acid activity, i.e., Alpha Value, of 2 to 5000, modified by precoking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 describes a process for the ethylation of toluene or ethylbenzene to produce p-ethyltoluene at a temperature of 350° C. to 550° C., a critical pressure of greater than one atmosphere and less than 400 psig, with hydrogen/ethylene ratio of 0.5 to 10 to reduce aging of the catalyst. The zeolite described in U.S. Pat. No. 4,117,024 has a crystal size greater than one micron, and is modified as the catalyst in U.S. Pat. No. 4,086,287 to attain the sorption capacity described in U.S. Pat. No. 4,086,287.

U.S. Pat. No. 4,117,026 describes the production of para-dialkyl benzenes having alkyls of 1 to 4 carbons under conditions which vary according to the feed. When the feed includes monoalkyl-substituted benzenes having an alkyl group of 1 to 4 carbons, olefins of 2 to 15 carbons, or paraffins of 3 to 60 carbons or mixtures thereof, conversion conditions include a temperature of 250° C. to 750°, a pressure of 0.1 to 100 atmospheres and a WHSV of 0.1 to 2000 hr$^{-1}$. For the disproportionation of toluene, the conditions include a temperature of 400° C. to 700° C., a pressure of 1 to 100 atmospheres and a WHSV of 1 to 50 hr$^{-1}$. When the feed includes olefins of 2 to 15 carbons including cyclic olefins, the conversion conditions include a temperature of 300° C. to 700° C., a pressure of 1 to 100 atmospheres and a WHSV of 1 to 1000 hr$^{-1}$. When the feed includes paraffins of 3 to 60 carbons, conditions include a temperature of 300° C. to 700° C., a pressure of 1 to 100 atmospheres and a WHSV of 0.1 to 100 hr$^{-1}$. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions include a temperature of 250° C. to 500° C. and a pressure greater than 200 psig. In the absence of added aromatics, the olefins and higher paraffins are more reactive and require lower severity of operation, e.g., a temperature of 250° C. to 600° C., preferably 300° C. to 550° C.

In general, therefore, catalytic conversion conditions over a catalyst comprising modified zeolite include a temperature of from about 100° C. to about 760° C., a pressure of from about 0.1 atmosphere (bar) to about 200 atmospheres (bar), a weight hourly space velocity of from about 0.08 to about 2000 hr$^{-1}$, and a hydrogen/organic, e.g., hydrocarbon, compound mole ratio of from 0 (no added hydrogen) to about 100.

The present invention is described in detail below in relation to the disproportionation of alkyl-substituted benzenes, particularly toluene, over a selectivated and optionally steamed catalyst comprising a crystalline material having the structure of PSH-3, MCM-22, or MCM-49, or a mixture of said materials. Normally a single pass conversion of an alkylbenzene stream results in a product stream which includes dialkylbenzenes having alkyl groups at all locations, i.e., o-, m-, and p-dialkylbenzenes. A catalyst treated in the manner described herein exhibits a desirable decreased o-dialkylbenzene sorption rate parameter and yields a significantly para-selected product from alkylbenzene disproportionation. For example, diffusion rate constants in toluene disproportionation have been discussed by Olson, D. H. et al., in "Structure-Selectivity Relationship in Xylene Isomerization and Selective Toluene Disproportionation", Catalytic Materials: Relationship Between Structure and Reactivity, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$. For high selectivity and catalytic efficiency it is desirable to have:

$$k_D << \frac{D_T}{r^2}.$$

The degree of para-selectivity depends on the activity and the diffusion characteristics of the catalyst. The primary product will be rich in the para isomer if initially produced m- and o-xylene diffuse out of the zeolite crystal at a rate $(D_{m,o}/r^2)$ that is lower than that of their conversion to p-xylene $(k_I)$, as well as lower than that of the p-xylene diffusion $(D_P/r^2)$ out of the catalyst, where:

$D_m$=diffusion of m-xylene;

$D_o$=diffusion of o-xylene;

$D_P$=diffusion of p-xylene;

r=length of diffusion path (crystal size);

$k_I$=rate of interconversion via isomerization of xylene isomers yielding secondary xylene product m-xylene and o-xylene.

It is desirable to increase the para-selectivity of the catalyst. Practically, this involves decreasing the o- and m-xylene diffusivities such that $$k_r > \frac{D_{m,o}}{r^2}.$$

In such a case the rate of conversion of m- and o-xylenes to p-xylene exceeds the diffusivities of the m- and o-xylenes. As a result, the proportion of the xylene yield that is p-xylene will be increased. Those skilled in the art will appreciate that similar considerations apply to the diffusivities of other alkylbenzenes. The invention also comprises the near regioselective conversion of alkylbenzene to para-dialkylbenzene by disproportionating alkylbenzene in a reaction stream containing an alkylbenzene feed with a selectivated and optionally steamed catalytic molecular sieve, optionally in the presence of hydrogen, and at reaction conditions suitable to provide p-dialkylbenzene selectivity of greater than about preferably greater than 90%. The production stream may also contain small amounts of o- and m-dialkylbenzene and trace amounts of impurities.

As used herein, the term "para-dialkylbenzene selectivity" means the proportion of p-dialkylbenzene, indicated as a percentage, among all of the dialkylbenzene products, i.e., p-dialkylbenzene, o-dialkylbenzene, and m-dialkylbenzene. Those skilled in the art will appreciate that the relative proximity of the boiling points of these isomers necessitates relatively expensive separation processes for the isolation of p-dialkylbenzene. On the other hand, p-dialkylbenzenes are more readily separated from other components in the product stream such as benzene, monoalkylbenzenes and other alkyl-substituted benzenes.

Furthermore, the dialkylbenzenes are known to proceed in reactions which produce unwanted heavier alkylbenzenes. For example, the xylenes can react to produce unwanted ethylbenzenes by the following reaction:

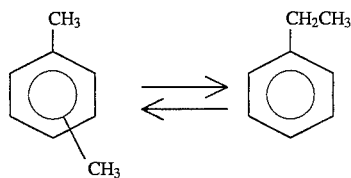

As explained in greater detail herein, the present invention provides a process for obtaining p-dialkylbenzenes at alkylbenzene conversion rates of at least 15%, preferably at least about 20–25%, with a p-dialkylbenzene selectivity of greater than 85%, preferably at least 90%.

The alkylbenzene feedstock preferably includes about 50% to 100% alkylbenzene, more preferably at least about 80% alkylbenzene. Other compounds such as benzene and other alkyl-substituted benzenes may also be present in the toluene feedstock without adversely affecting the present invention.

The alkylbenzene feedstock may also be dried, if desired, in a manner which will minimize moisture entering the reaction zone. Numerous methods known in the art are suitable for drying the alkylbenzene charge for the process of the invention. These methods include percolation through any suitable desiccant, for example, silica gel, activated alumina, molecular sieves or other suitable substances, or the use of liquid charge dryers.

The crystal size of zeolites used herein is preferably greater than 0.1 micron. The accurate measurement of crystal size of zeolite materials is frequently very difficult. Microscopy methods such as SEM and TEM are often used, but these methods require measurements on a large number of crystals and for each crystal measured, values may be required in up to three dimensions. For the zeolite materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by Crank, J., *The Mathematics of Diffusion,* Oxford at the Clarendon Press, 52–56 (1957) for the rate of sorbate uptake by a solid whose diffusion properties can be approximated by a plane sheet model. In addition, the diffusion constant of 2,2-dimethylbutane, D, under these conditions is taken to be $1.5 \times 10^{-14}$ cm$^2$/sec. The relation between crystal size measured in microns, d, and diffusion time measured in minutes, $t_{0.3}$, the time required for the uptake of 30% of capacity of hydrocarbon, is:

$$d = 0.0704 \times t_{0.3}^{1/2}.$$

In the present case these measurements have been made on a computer controlled, thermogravimetric electrobalance, but there are numerous ways one skilled in the art could obtain the data. The larger crystal material used herein has a sorption time, $t_{0.3}$, of 497 minutes, which gives a calculated crystal size of 1.6 microns. The smaller crystal material has a sorption time of 7.8 minutes, and a calculated crystal size of 0.20 micron.

Operating conditions employed in the process of the present invention will affect the para-selectivity and alkylbenzene conversion rate. Such conditions include the temperature, pressure, space velocity, molar ratio of the reactants, and the hydrogen to hydrocarbon mole ratio ($H_2$/HC). For example, it has been observed that an increase in temperature can increase the activity of the modified catalyst. It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst.

A selectivated and steamed catalytic molecular sieve may be contacted with an alkylbenzene feedstock under conditions for effecting vapor-phase disproportionation. Conditions effective for accomplishing the high para-selectivity and acceptable alkylbenzene disproportionation conversion rates include a reactor inlet temperature of from about 200° C. to about 600° C., preferably from about 350° C. to about 500° C.; a pressure of from about atmospheric to about 5000 psig, preferably from about 100 to about 1000 psig; a WHSV of from about 0.1 to about 20 hr$^{-1}$, preferably from about 2 to about 10 hr$^{-1}$; and a $H_2$/HC mole ratio of from about 0.05 to about 20, preferably from about 0.1 to about 6. This process may be conducted in either batch or fluid bed operation, with the attendant benefits of either operation readily obtainable. The effluent may be separated and distilled to remove the desired product, i.e., the para-isomer, as well as other by-products. Alternatively, the appropriate fraction may be subjected to further separation, in the case of xylenes, subjected to the PAREX process or crystallization to yield p-xylene.

The catalyst may be further modified in order to reduce the amount of undesirable by-products, such as, in the case of xylenes, ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to between about 3% and 4%. This level of ethylbenzene is unacceptable for polymer grade p-xylene since ethylbenzene in the $C_8$ product, if not removed, degrades the quality of fibers ultimately produced from the p-xylene product. Consequently, ethylbenzene content of the p-xylene fraction must be kept low. Ethylbenzene can be substantially removed by crystallization, isomerization or by superfractionation processes. Removal of the ethylbenzene by conventional isomerization is impractical when the xylene stream includes greater than 70% or 80% p-xylene, since the p-xylene would be concurrently isomerized to equilibrium xylenes, thereby reducing the amount of p-xylene in the xylene stream. It is known in the art that the alternative procedure of removing the ethylbenzene by superfractionation is extremely expensive.

In order to avoid the need for downstream ethylbenzene removal, the level of ethylbenzene by-product is advantageously reduced by incorporating a hydrogenation/dehydrogenation function within the catalyst, such as by addition of a metal compound such as platinum. While platinum is the preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.01% to about 2%, typically about 0.5%. It is desirable that the metal be able to enter the pores of the catalyst. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The metallic compound advantageously enters the pores of the catalyst. The catalyst can then be filtered, washed with water and calcined at temperatures of from about 250° C. to about 500° C. It will be appreciated by those skilled in the art that similar considerations apply to processes involving alkylbenzenes other than toluene.

The following examples will serve to illustrate the present invention without unduly limiting same. In these examples we have examined the process, with and without selectivation treatment of the catalyst. In-situ selectivation treatments were conducted, and ex-situ treatments were performed as described in U.S. Pat. Nos. 4,090,981; 4,447,583; and 4,465,886, each incorporated herein by reference in its entirety.

Toluene disproportionation experiments were conducted in an automated unit with on-line sampling. In these experiments, approximately 1 gram of catalyst (⅛-inch extrudate) was loaded into a 0.25 inch diameter stainless steel tube reactor. The catalyst was heated to 538° C. in 200 cc/minute air at a heating rate of 2° C./minute in each instance.

EXAMPLE 1

A sample of MCM-49 in the hydrogen form, i.e., HMCM-49, having a crystal size of 0.1–0.5 micron, an Alpha Value of about 450, and a p-xylene sorption capacity of about 10 grams/100 grams was mixed with alumina binder to provide a catalyst comprising 65 wt. % HMCM-49 and 35 wt. % alumina. The mixture was used to prepare ¹⁄₁₆-inch extrudate catalyst for use in the present process.

EXAMPLE 2

A sample of MCM-22 in the hydrogen form, i.e., HMCM-22, having a crystal size of 0.1–0.5 micron, an Alpha Value of about 450, and a p-xylene sorption capacity of about 10 grams/100 grams was mixed with alumina binder to provide a catalyst comprising 65 wt. % HMCM-22 and 35 wt. % alumina. The mixture was used to prepare ¹⁄₁₆-inch extrudate catalyst for use in the present process.

EXAMPLE 3

A sample of MCM-22 in the hydrogen form, i.e., HMCM-22, having a crystal size of 0.1–0.5 micron, an Alpha Value of about 450, and a p-xylene sorption capacity of about 10 grams/100 grams was mixed with silica binder to provide a catalyst comprising 65 wt. % HMCM-22 and 35 wt. % silica. The mixture was used to prepare ¹⁄₁₆-inch extrudate catalyst for use in the present process.

EXAMPLE 4

This toluene disproportionation experiment involved the catalyst prepared in Example 1. Following the heating activation step described above, the experiment was initiated with pure toluene feed at 424° C., 4 hr$^{-1}$ WHSV, 2 $H_2$/HC mole ratio, and 500 psig. As shown in Table G, the catalyst was active and produced 24% para-xylene product at 20% conversion. A temperature scan at 4 hr$^{-1}$ WHSV, 2 $H_2$/HC mole ratio, and 500 psig showed that the catalyst produced near equilibrium para-xylene product under these conditions at all temperatures between 424° C. and 505° C. A WHSV scan at 464° C. also showed near equilibrium para-xylene at conversions between 8 and 46%. At this point, a toluene feed containing 1.0 wt. % of dimethylphenylmethylpolysiloxane (Dow-550) was admitted to the reactor at 485° C., 4 hr$^{-1}$ WHSV, 2 $H_2$/HC mole ratio, and 500 psig.

An examination of the selectivity/conversion data (Table G) shows a rapid increase in selectivity over about 20 hours on stream. For example, after 7 hours of selectivation, the catalyst produced 56% para-xylene product at 7% conversion. This selectivity is far higher than an equilibrium distribution of xylene products and much more selective than the parent material at comparable conversion. Thus, the treatment with the silicone compound increased the shape selectivity of the disproportionation reaction.

To determine the level of permanence of the selectivation, the catalyst was regenerated by heating in air to 538° C. at a rate of 2° C./minute. After regeneration, the initial sample taken at 485° C., 4 hr$^{-1}$ WHSV, 2 $H_2$/HC mole ratio, and 500 psig on pure toluene feed showed 26% para-xylene product at 15% conversion. Thus, the catalyst displayed a decrease in selectivity after the regeneration; however, it still displayed enhanced selectivity compared to the parent catalyst material. Losses in selectivity of in-situ selectivated, alumina-bound catalysts after regeneration have been commonly observed for prior art catalysts in the process of toluene disproportionation.

In Table G, samples 1–10 involved pure toluene feed, samples 11–16 involved the feed having DOW-550 added, and samples 18–19 involved pure toluene feed.

TABLE G

| Sample | 1 | 2 | 3 | 4 | 5 | 6 | 7 | 8 | 9 | 10 |
|---|---|---|---|---|---|---|---|---|---|---|
| Temp, °C. | 424.70 | 444.70 | 464.60 | 484.40 | 505.40 | 464.60 | 464.60 | 464.60 | 464.80 | 465.50 |
| Pressure, psig | 494.30 | 496.30 | 496.00 | 495.50 | 500.20 | 499.00 | 504.00 | 501.20 | 503.50 | 507.20 |
| WHSV, hr$^{-1}$ | 4.00 | 4.00 | 4.00 | 4.00 | 4.00 | 2.00 | 4.00 | 8.00 | 16.00 | 32.00 |
| $H_2$/HC (mol) | 1.99 | 1.99 | 1.99 | 1.99 | 1.99 | 1.99 | 1.99 | 2.00 | 2.00 | 2.00 |
| TOS, hours | 4.40 | 7.10 | 11.17 | 13.87 | 17.93 | 20.63 | 24.70 | 27.40 | 31.47 | 34.17 |
| $C_5$— | 0.29 | 0.66 | 1.11 | 1.60 | 2.31 | 1.49 | 0.61 | 0.29 | 0.06 | 0.04 |
| Benzene | 8.68 | 11.97 | 15.53 | 18.59 | 21.49 | 19.48 | 14.87 | 10.02 | 5.98 | 3.52 |
| Toluene | 79.58 | 72.21 | 63.81 | 56.37 | 50.25 | 53.94 | 65.20 | 76.71 | 86.33 | 91.95 |
| Ethylbenzene | 0.06 | 0.13 | 0.25 | 0.44 | 0.57 | 0.41 | 0.17 | 0.06 | 0.00 | 0.00 |

TABLE G-continued

| | | | | | | | | | |
|---|---|---|---|---|---|---|---|---|---|
| p-Xylene | 2.66 | 3.41 | 4.19 | 4.84 | 5.21 | 5.25 | 4.25 | 2.97 | 1.82 | 1.11 |
| m-Xylene | 5.82 | 7.47 | 9.20 | 10.69 | 11.42 | 11.53 | 9.35 | 6.55 | 3.98 | 2.38 |
| o-Xylene | 2.43 | 3.20 | 4.06 | 4.75 | 5.23 | 5.06 | 4.11 | 2.84 | 1.70 | 1.00 |
| Ethyltoluene | 0.25 | 0.36 | 0.49 | 0.57 | 0.62 | 0.51 | 0.32 | 0.18 | 0.05 | 0.00 |
| Trimethylbenzene | 0.23 | 0.59 | 1.23 | 1.95 | 2.62 | 2.11 | 1.02 | 0.38 | 0.08 | 0.00 |
| Diethylbenzene | 0.00 | 0.00 | 0.12 | 0.20 | 0.29 | 0.21 | 0.11 | 0.00 | 0.00 | 0.00 |
| Dimethylethylbenzene | 0.00 | 0.00 | 0.00 | 0.00 | 0.00 | 0.00 | 0.00 | 0.00 | 0.00 | 0.00 |
| Tetramethylbenzene | 0.00 | 0.00 | 0.00 | 0.00 | 0.00 | 0.00 | 0.00 | 0.00 | 0.00 | 0.00 |
| Other | 0.00 | 0.00 | 0.00 | 0.00 | 0.00 | 0.00 | 0.00 | 0.00 | 0.00 | 0.00 |
| p-Xylene (X) | 24.40 | 24.24 | 24.01 | 23.87 | 23.83 | 24.05 | 24.00 | 24.01 | 24.28 | 24.77 |
| m-Xylene (X) | 53.32 | 53.06 | 52.73 | 52.73 | 52.24 | 52.78 | 52.77 | 53.04 | 53.07 | 53.04 |
| o-Xylene (X) | 22.28 | 22.70 | 23.26 | 23.40 | 23.94 | 23.17 | 23.23 | 22.95 | 22.65 | 22.19 |
| p-Xylene (E) | 104.09 | 103.42 | 102.45 | 101.85 | 101.64 | 102.60 | 102.38 | 102.45 | 103.59 | 105.69 |
| m-Xylene (E) | 102.28 | 101.78 | 101.15 | 101.14 | 100.21 | 101.25 | 101.23 | 101.74 | 101.80 | 101.74 |
| o-Xylene (E) | 91.21 | 92.92 | 95.20 | 95.78 | 97.98 | 94.85 | 95.08 | 93.95 | 92.71 | 90.83 |
| Toluene conv. | 20.41 | 27.78 | 36.19 | 43.63 | 49.74 | 46.06 | 34.08 | 23.29 | 13.67 | 8.05 |
| Benzene/xylene (mol) | 1.08 | 1.16 | 1.21 | 1.25 | 1.34 | 1.21 | 1.14 | 1.10 | 1.08 | 1.07 |

| Sample | 11 | 12 | 13 | 14 | 15 | 16 | 17 | 18 |
|---|---|---|---|---|---|---|---|---|
| Temp, °C. | 485.40 | 485.60 | 485.60 | 484.70 | 484.70 | 484.70 | 484.90 | 484.70 |
| Pressure, psig | 500.70 | 507.00 | 499.00 | 498.70 | 498.00 | 499.00 | 494.70 | 497.20 |
| WHSV, hr$^{-1}$ | 4.00 | 4.00 | 4.00 | 4.00 | 4.00 | 4.00 | 4.00 | 4.00 |
| H$_2$/HC (mol) | 1.99 | 1.99 | 1.99 | 1.99 | 1.99 | 1.99 | 1.99 | 1.99 |
| TOS, hours | 36.92 | 39.63 | 43.70 | 47.75 | 51.82 | 55.88 | 61.32 | 64.03 |
| C$_5$— | 3.99 | 3.60 | 1.84 | 1.18 | 0.95 | 0.06 | 2.18 | 1.22 |
| Benzene | 18.57 | 6.54 | 2.29 | 2.04 | 1.99 | 1.93 | 6.20 | 9.40 |
| Toluene | 52.82 | 79.98 | 92.98 | 94.34 | 94.74 | 95.15 | 84.60 | 77.53 |
| Ethylbenzene | 0.58 | 0.14 | 0.00 | 0.00 | 0.00 | 0.00 | 0.15 | 0.18 |
| p-Xylene | 5.13 | 3.90 | 1.62 | 1.45 | 1.42 | 1.37 | 1.50 | 2.54 |
| m-Xylene | 11.20 | 4.53 | 1.14 | 0.92 | 0.85 | 0.83 | 3.01 | 5.47 |
| o-Xylene | 4.99 | 0.92 | 0.12 | 0.07 | 0.06 | 0.06 | 1.34 | 2.43 |
| Ethyltoluene | 0.67 | 0.29 | 0.00 | 0.00 | 0.00 | 0.00 | 0.74 | 0.63 |
| Trimethylbenzene | 1.86 | 0.10 | 2.62 | 2.11 | 0.00 | 0.00 | 0.29 | 0.60 |
| Diethylbenzene | 0.20 | 0.00 | 0.29 | 0.21 | 0.00 | 0.00 | 0.00 | 0.00 |
| Dimethylethylbenzene | 0.00 | 0.00 | 0.00 | 0.00 | 0.00 | 0.00 | 0.00 | 0.00 |
| Tetramethylbenzene | 0.00 | 0.00 | 0.00 | 0.00 | 0.00 | 0.00 | 0.00 | 0.00 |
| Other | 0.00 | 0.00 | 0.00 | 0.00 | 0.00 | 0.00 | 0.00 | 0.00 |
| p-Xylene (X) | 24.05 | 41.73 | 56.26 | 59.44 | 60.86 | 60.71 | 25.62 | 24.31 |
| m-Xylene (X) | 52.54 | 48.46 | 39.67 | 37.63 | 36.72 | 36.65 | 51.42 | 52.40 |
| o-Xylene (X) | 23.41 | 9.81 | 4.07 | 2.93 | 2.42 | 2.64 | 22.96 | 23.29 |
| p-Xylene (E) | 102.62 | 178.02 | 240.03 | 253.58 | 259.65 | 258.99 | 109.32 | 103.72 |
| m-Xylene (E) | 100.79 | 92.97 | 76.10 | 72.19 | 70.43 | 70.30 | 98.63 | 100.52 |
| o-Xylene (E) | 95.81 | 40.15 | 16.64 | 11.99 | 9.91 | 10.82 | 93.98 | 95.32 |
| Toluene conv. | 47.18 | 20.02 | 7.01 | 5.66 | 5.26 | 4.85 | 15.40 | 22.47 |
| Benzene/xylene (mol) | 1.18 | 0.95 | 1.08 | 1.14 | 1.16 | 1.16 | 1.44 | 1.22 |

EXAMPLE 5

In this experiment, the parent HMCM-22/Al$_2$O$_3$ material of Example 2 was subjected to an impregnation/calcination procedure with Dow-550 silicone as follows.

To 2.0 grams of the HMCM-22/Al$_2$O$_3$ extrudate was added 0.3927 grams of Dow-550 dissolved in 20 grams of hexane. The catalyst was agitated in the silicone solution for several minutes and the hexane distilled off by high vacuum distillation. The dry catalyst was then calcined at 1°/minute in nitrogen to 538° C. After allowing the sample to cool to room temperature, the sample was then calcined in air at 1°/minute to 538° C. and held for 3 hours. The silica-modified catalyst had gained 6.46 wt. %, presumably as SiO$_2$.

After catalyst activation as described above, the experiment was initiated with pure toluene feed at 424° C., 4 hr$^{-1}$ WHSV, 2 H$_2$/HC mole ratio, and 500 psig. As shown in Table H, the catalyst was active and produced 24% para-xylene product at 27% conversion. A temperature scan at 4 hr$^{-1}$ WHSV, 2 H$_2$/HC mole ratio, and 500 psig showed that the catalyst produced near equilibrium para-xylene product under these conditions at all temperatures between 424° C. and 505° C. At this point, a toluene feed containing 0.5 wt. % of dimethylphenylmethylpolysiloxane (Dow-550) was admitted to the reactor at 485° C., 4 hr$^{-1}$ WHSV, 2 H$_2$/HC mole ratio, and 500 psig.

An examination of the selectivity/conversion data (Table H) shows a rapid increase in selectivity over about 13 hours on stream, at which point the catalyst produced 62% para-xylene product at 11% conversion. This selectivity, as indicated above, is far higher than an equilibrium distribution of xylene products and much more than that of the parent material at comparable conversion. Thus, the treatment with silicone has increased the shape selectivity of the disproportionation reaction.

To determine the level of permanence of the selectivation, the catalyst was regenerated as in Example 4. After regeneration, the initial sample taken at 485° C., 4 hr$^{-1}$ WHSV, 2 H$_2$/HC mole ratio, and 500 psig on pure toluene feed showed 27% para-xylene at 14% conversion; however, it still displayed enhanced selectivity compared to the parent material. Thus, the catalyst displayed a decrease in selectivity after the regeneration. Losses in selectivity of in-situ selectivated, alumina-bound catalysts after regeneration have been commonly observed for prior art catalysts in the process of toluene disproportionation.

In Table H, samples 1–5 involved pure toluene feed, samples 6–10 involved the feed having DOW-550 added, and samples 11–13 involved pure toluene feed.

TABLE H

| Sample | 1 | 2 | 3 | 4 | 5 | 6 | 7 | 8 |
|---|---|---|---|---|---|---|---|---|
| Temp, °C. | 425.40 | 445.20 | 465.30 | 484.90 | 504.70 | 484.90 | 484.90 | 484.90 |
| Pressure, psig | 497.70 | 497.50 | 498.00 | 499.70 | 501.50 | 503.20 | 502.70 | 503.00 |
| WHSV, $hr^{-1}$ | 4.00 | 4.00 | 4.00 | 4.00 | 4.00 | 4.00 | 4.00 | 4.00 |
| $H_2$/HC (mol) | 2.00 | 2.00 | 2.00 | 2.00 | 2.00 | 2.00 | 2.00 | 2.00 |
| TOS, hours | 2.72 | 6.78 | 10.83 | 10.83 | 18.97 | 21.70 | 24.40 | 28.47 |
| $C_5$— | 0.59 | 0.88 | 1.24 | 1.62 | 2.11 | 3.55 | 4.35 | 2.99 |
| Benzene | 11.50 | 13.77 | 16.20 | 18.31 | 20.09 | 18.21 | 15.2 | 17.37 |
| Toluene | 73.03 | 66.94 | 61.65 | 56.65 | 53.75 | 54.87 | 58.22 | 78.25 |
| Ethylbenzene | 0.14 | 0.21 | 0.31 | 0.40 | 0.47 | 0.54 | 0.52 | 0.19 |
| p-Xylene | 3.36 | 4.05 | 4.50 | 4.95 | 5.21 | 4.92 | 4.94 | 4.96 |
| m-Xylene | 7.30 | 8.82 | 9.85 | 10.78 | 11.33 | 10.68 | 10.38 | 4.74 |
| o-Xylene | 3.09 | 3.82 | 4.30 | 4.81 | 5.03 | 4.75 | 4.45 | 1.07 |
| Ethyltoluene | 0.35 | 0.45 | 0.51 | 0.53 | 0.53 | 0.73 | 0.85 | 0.37 |
| Trimethylbenzene | 0.63 | 0.96 | 1.31 | 1.68 | 1.97 | 1.58 | 0.96 | 0.09 |
| Diethylbenzene | 0.00 | 0.10 | 0.13 | 0.17 | 0.21 | 0.16 | 0.10 | 0.00 |
| Dimethylethylbenzene | 0.00 | 0.00 | 0.00 | 0.00 | 0.00 | 0.00 | 0.00 | 0.00 |
| Tetramethylbenzene | 0.00 | 0.00 | 0.00 | 0.00 | 0.00 | 0.00 | 0.00 | 0.00 |
| Other | 0.00 | 0.00 | 0.00 | 0.00 | 0.00 | 0.00 | 0.00 | 0.00 |
| p-Xylene (X) | 24.42 | 24.28 | 24.10 | 24.12 | 24.16 | 24.18 | 25.00 | 46.05 |
| m-Xylene (X) | 53.08 | 52.85 | 52.83 | 52.46 | 52.53 | 52.49 | 52.51 | 44.02 |
| o-Xylene (X) | 22.50 | 22.87 | 23.07 | 23.42 | 23.31 | 23.33 | 22.49 | 9.94 |
| p-Xylene (E) | 104.18 | 103.59 | 102.83 | 102.89 | 103.08 | 103.18 | 106.66 | 196.44 |
| m-Xylene (E) | 101.82 | 101.38 | 101.33 | 100.63 | 100.77 | 100.68 | 100.72 | 84.44 |
| o-Xylene (E) | 92.12 | 93.61 | 94.44 | 95.88 | 95.40 | 95.49 | 92.08 | 40.67 |
| Toluene conv. | 26.97 | 33.06 | 38.35 | 43.25 | 46.95 | 45.13 | 41.78 | 21.75 |
| Benzene/xylene (mol) | 1.14 | 1.12 | 1.18 | 1.21 | 1.27 | 1.22 | 1.05 | 0.93 |

| Sample | 9 | 10 | 11 | 12 | 13 |
|---|---|---|---|---|---|
| Temp, °C. | 484.90 | 485.10 | 425.40 | 445.40 | 465.30 |
| Pressure, psig | 502.70 | 504.20 | 498.00 | 497.20 | 502.70 |
| WHSV, $hr^{-1}$ | 4.00 | 4.00 | 4.00 | 4.00 | 4.00 |
| $H_2$/HC (mol) | 2.00 | 2.00 | 2.00 | 2.00 | 2.00 |
| TOS, hours | 31.18 | 35.23 | 38.43 | 41.13 | 43.70 |
| $C_5$— | 3.32 | 2.49 | 0.49 | 0.79 | 0.79 |
| Benzene | 5.16 | 3.71 | 5.89 | 7.84 | 7.84 |
| Toluene | 84.90 | 89.00 | 86.21 | 81.64 | 81.64 |
| Ethylbenzene | 0.00 | 0.00 | 0.00 | 0.97 | 0.07 |
| p-Xylene | 3.75 | 2.91 | 1.90 | 2.37 | 2.37 |
| m-Xylene | 2.43 | 1.63 | 3.76 | 4.79 | 4.79 |
| o-Xylene | 0.29 | 0.16 | 1.53 | 2.00 | 2.00 |
| Ethyltoluene | 0.15 | 0.11 | 0.22 | 0.29 | 0.29 |
| Trimethylbenzene | 0.00 | 0.00 | 0.08 | 0.22 | 0.22 |
| Diethylbenzene | 0.00 | 0.00 | 0.00 | 0.00 | 0.00 |
| Dimethylethylbenzene | 0.00 | 0.00 | 0.00 | 0.00 | 0.00 |
| Tetramethylbenzene | 0.00 | 0.00 | 0.00 | 0.00 | 0.00 |
| Other | 0.00 | 0.00 | 0.00 | 0.00 | 0.00 |
| p-Xylene (X) | 57.95 | 61.97 | 26.50 | 25.84 | 25.44 |
| m-Xylene (X) | 37.55 | 34.72 | 52.27 | 52.30 | 22.21 |
| o-Xylene (X) | 4.51 | 3.31 | 21.23 | 21.86 | 4.07 |
| p-Xylene (E) | 247.21 | 264.38 | 113.06 | 110.24 | 108.51 |
| m-Xylene (E) | 72.02 | 66.60 | 100.26 | 100.33 | 100.42 |
| o-Xylene (E) | 18.46 | 13.55 | 86.91 | 89.46 | 90.93 |
| Toluene conv. | 15.09 | 10.99 | 13.78 | 18.35 | 22.51 |
| Benzene/xylene (mol) | 1.08 | 1.08 | 1.11 | 1.16 | 51.21 |

EXAMPLE 6

This toluene disproportionation experiment involved the catalyst prepared in Example 3. Following the heating activation step described above, the experiment was initiated with pure toluene feed at 485° C., 4 $hr^{-1}$ WHSV, 2 $H_2$/HC mole ratio, and 500 psig. As shown in Table I, the catalyst was active and produced 24% para-xylene product at 47% conversion.

After 19 hours on stream, a toluene feed containing 1.0 wt. % of dimethylphenylmethylpolysiloxane (Dow-500) was admitted to the reactor at 485° C., 4 $hr^{-1}$ WHSV, 2 $H_2$/HC, mole ratio, and 500 psig.

An examination of the selectivity/conversion data (Table I) shows an increase in selectivity over about 22 hours on stream. For example, after 19 hours of selectivation, the catalyst produced 44% para-xylene product at 24% conversion. Thus, the treatment with the silicone compound increased the shape selectivity of the disproportionation reaction.

In Table I, samples 1–7 involved pure toluene feed and samples 8–13 involved the feed having DOW-550 added.

TABLE I

| Sample | 1 | 2 | 3 | 4 | 5 | 6 | 7 | 8 | 9 | 10 | 11 | 12 | 13 |
|---|---|---|---|---|---|---|---|---|---|---|---|---|---|
| Temp, °C. | 485.40 | 485.10 | 485.40 | 485.40 | 485.10 | 485.10 | 485.10 | 485.10 | 485.10 | 485.10 | 485.10 | 485.10 | 485.10 |
| Pressure, psig | 503.70 | 498.30 | 497.70 | 505.00 | 498.30 | 500.70 | 501.50 | 502.70 | 488.00 | 485.20 | 485.00 | 492.00 | 513.00 |
| WHSV, hr$^{-1}$ | 3.99 | 3.99 | 3.99 | 3.99 | 3.99 | 3.99 | 3.99 | 3.99 | 3.99 | 3.99 | 3.99 | 3.99 | 3.99 |
| H$_2$/HC (mol) | 2.00 | 2.00 | 2.00 | 2.00 | 2.00 | 2.00 | 2.00 | 2.00 | 2.00 | 2.00 | 2.00 | 2.00 | 2.00 |
| TOS, hours | 2.70 | 5.40 | 10.83 | 13.55 | 16.25 | 18.95 | 22.77 | 25.50 | 29.55 | 33.62 | 37.68 | 41.75 | 46.02 |
| C$_5$— | 2.29 | 1.96 | 1.47 | 1.43 | 1.49 | 1.47 | 2.98 | 3.32 | 3.18 | 12.75 | 2.55 | 2.29 | 12.92 |
| Benzene | 19.84 | 19.67 | 19.35 | 19.13 | 19.67 | 19.74 | 18.75 | 15.20 | 11.91 | 0.00 | 8.72 | 7.99 | 0.00 |
| Toluene | 53.32 | 53.58 | 54.16 | 54.09 | 53.78 | 53.78 | 52.63 | 58.86 | 67.41 | 72.85 | 76.66 | 78.56 | 71.27 |
| Ethylbenzene | 0.51 | 0.45 | 0.39 | 0.38 | 0.34 | 0.34 | 0.49 | 0.46 | 0.31 | 0.21 | 0.14 | 0.11 | 0.19 |
| p-Xylene | 5.12 | 5.21 | 5.30 | 5.40 | 5.34 | 5.34 | 5.52 | 5.69 | 5.92 | 5.60 | 5.03 | 4.70 | 3.46 |
| m-Xylene | 11.17 | 11.4 | 11.70 | 11.88 | 11.84 | 11.84 | 12.22 | 11.65 | 8.88 | 6.96 | 5.70 | 5.25 | 7.50 |
| o-Xylene | 5.00 | 5.11 | 5.21 | 5.31 | 5.24 | 5.27 | 5.40 | 3.74 | 1.80 | 1.20 | 0.87 | 0.75 | 3.36 |
| Ethyltoluene | 0.62 | 0.54 | 0.48 | 0.45 | 0.42 | 0.41 | 0.62 | 0.66 | 0.49 | 0.37 | 0.27 | 0.23 | 0.51 |
| Trimethylbenzene | 1.87 | 1.81 | 1.76 | 1.74 | 1.67 | 1.64 | 1.26 | 0.35 | 0.12 | 0.06 | 0.04 | 0.03 | 0.64 |
| Diethylbenzene | 0.23 | 0.21 | 0.19 | 0.18 | 0.17 | 0.17 | 0.12 | 0.05 | 0.00 | 0.00 | 0.00 | 0.00 | 0.00 |
| Dimethylethylbenzene | 0.03 | 0.00 | 0.00 | 0.00 | 0.00 | 0.00 | 0.00 | 0.00 | 0.00 | 0.00 | 0.00 | 0.00 | 0.15 |
| Tetramethylbenzene | 0.00 | 0.00 | 0.00 | 0.00 | 0.00 | 0.00 | 0.00 | 0.00 | 0.00 | 0.00 | 0.00 | 0.00 | 0.00 |
| Other | 0.00 | 0.00 | 0.00 | 0.00 | 0.00 | 0.00 | 0.00 | 0.00 | 0.00 | 0.00 | 0.00 | 0.00 | 0.00 |
| p-Xylene (X) | 24.04 | 23.92 | 23.84 | 23.90 | 23.84 | 23.79 | 23.85 | 27.00 | 35.68 | 40.71 | 43.36 | 43.94 | 24.16 |
| m-Xylene (X) | 52.47 | 52.62 | 52.70 | 52.58 | 52.76 | 52.74 | 52.81 | 55.24 | 53.48 | 50.54 | 49.13 | 49.09 | 52.37 |
| o-Xylene (X) | 23.50 | 23.46 | 23.46 | 23.52 | 23.40 | 23.47 | 23.34 | 17.65 | 10.84 | 8.75 | 7.51 | 6.97 | 23.47 |
| p-Xylene (E) | 102.54 | 102.05 | 101.72 | 101.95 | 101.51 | 101.51 | 101.75 | 115.17 | 152.22 | 173.66 | 185.00 | 187.45 | 103.08 |
| Toluene conv. | 46.68 | 46.42 | 45.84 | 45.91 | 46.16 | 46.22 | 47.37 | 41.13 | 32.59 | 27.15 | 23.34 | 21.44 | 28.73 |
| Benzene/xylene (mol) | 1.27 | 1.23 | 1.18 | 1.15 | 1.19 | 1.20 | 1.10 | 0.98 | 0.98 | 0.00 | 1.02 | 1.01 | 0.00 |

What is claimed is:

1. A process for selective production of para-dialkyl substituted benzene which comprises converting a feedstock comprising (1) mono-alkyl substituted benzene having an alkyl group of from 1 to 4 carbon atoms, or (2) a mixture of said mono-alkyl substituted benzene or benzene with an alkylating agent containing from 1 to 4 carbon atoms, to product comprising para-dialkyl substituted benzene containing alkyl groups of 1 to 4 carbons at conversion conditions with a catalyst comprising a porous crystalline material having the structure of MCM-49, said crystalline material having been treated with one or a combination of selectivating agent compounds selected from the group consisting of silicones, Siloxanes having at least two siloxane units, and silanes, whereby the treated crystalline material has an Alpha Value of from about 10 to about 2000, a p-xylene sorption capacity greater than about 1 gram/100 grams of crystalline material, said sorption capacity being measured at 120° C. and a p-xylene pressure of 4.5±0.8 mm of mercury.

2. The process of claim 1 wherein said conversion conditions include a temperature of from about 100° C. to about 760° C., a pressure of from about 0.1 atmosphere to about 200 atmospheres, a weight hourly space velocity of from about 0.08 hr$^{-1}$ to about 2000 hr$^{-1}$ and an added hydrogen/hydrocarbon mole ratio of from 0 to about 100.

3. The process of claim 1 wherein said crystalline material treatment comprises contacting said crystalline material with one or a combination of said selectivating agent compounds and then calcining the contacted crystalline material.

4. The process of claim 3 wherein said selectivating agent compound is a siloxane characterized by the formula:

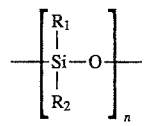

wherein $R_1$ and $R_2$ are independently hydrogen; halogen; hydroxyl; alkyl of from 1 to 10 carbons; halogenated alkyl of from 1 to 10 carbons; aryl, aralkyl, or alkaryl of from 6 to 20 carbons; halogenated aryl, aralkyl, or alkaryl of from 6 to 20 carbons; or mixtures thereof, and n is an integer of from 2 to 1000.

5. The process of claim 3 wherein said selectivating agent compound is selected from the group consisting of dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, ethylvinyl silicone, hexamethyl cyclotrisiloxane, octamethyl cyclotetrasiloxane, hexaphenyl cyclotrisiloxane and octaphenyl cyclotetrasiloxane, and mixtures thereof.

6. The process of claim 3 wherein said selectivating agent compound is a silane characterized by the formula:

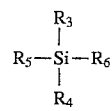

where $R_3$, $R_4$, $R_5$ and $R_6$ are independently selected from the group consisting of hydrogen; hydroxyl; halogen; alkyl of from 1 to 10 carbons; halogenated alkyl of from 1 to 10 carbons; alkoxy of from 1 to 10 carbons; aryl, aralkyl, or alkaryl of from 6 to 20 carbons; halogenated aryl, aralkyl, or alkaryl of from 6 to 20 carbons; organoamine of 3 to 9 carbons; or mixtures thereof.

7. The process of claim 6 wherein said $R_3$, $R_4$, $R_5$, and $R_6$ are independently selected from the group consisting of —N$^+$(CH$_3$)$_3$, —N$^+$(C$_2$H$_5$)$_3$, —N$^+$(C$_3$H$_7$)$_3$, and mixtures thereof.

8. The process of claim 3 wherein said contacting is repeated from 2 to 6 times.

9. The process of claim 4 wherein said contacting is repeated from 2 to 6 times.

10. The process of claim 5 wherein said contacting is repeated from 2 to 6 times.

11. The process of claim 6 wherein said contacting is repeated from 2 to 6 times.

12. The process of claim 7 wherein said contacting is repeated from 2 to 6 times.

13. The process of claim 3 wherein said calcination comprises heating the contacted crystalline material at a temperature of from greater than about 200° C. to about 600° C. for from about 1 hour to about 24 hours.

14. The process of claim 3 wherein said treated crystalline material is ion exchanged with cations selected from the group consisting of metals, hydrogen, hydrogen precursors, and combinations thereof.

15. The process of claim 3 wherein said treated crystalline material is steamed at a temperature of from about 100° C. to about 600° C. and a pressure of from about 0.01 psia to about 50 psia.

16. The process of claim 14 wherein said ion exchanged crystalline material is steamed at a temperature of from about 100° C. to about 600° C. and a pressure of from about 0.01 psia to about 50 psia.

17. The process of claim 1 wherein said feedstock comprises mono-alkyl substituted benzene having an alkyl group of 1 to 4 carbon atoms and said conversion conditions include a temperature of from about 200° C. to about 600° C., a pressure of from atmospheric to about 5000 psig, a weight hourly space velocity of from about 0.1 $hr^{-1}$ to about 20 $hr^{-1}$, and an added hydrogen/hydrocarbon mole ratio of from about 0.05 to about 20.

* * * * *